US005501984A

United States Patent [19]
Hofstetter et al.

[11] Patent Number: 5,501,984
[45] Date of Patent: Mar. 26, 1996

[54] ANALYSER UNIT FOR HETEROGENEOUS IMMUNOLOGICAL TESTS

[75] Inventors: Meinrad Hofstetter, Felsberg; Klaus Leckebusch, Masein; Armin Panzer, Trin, all of Switzerland

[73] Assignee: Boehringer Mannheim GmbH, Mannheim, Germany

[21] Appl. No.: 77,500

[22] Filed: Jun. 17, 1993

Related U.S. Application Data

[62] Division of Ser. No. 874,996, Apr. 24, 1992, abandoned, which is a continuation of Ser. No. 551,827, Jul. 12, 1990, abandoned.

[30] Foreign Application Priority Data

Jul. 19, 1989 [DE] Germany .......................... 39 23 833.4

[51] Int. Cl.⁶ ................................................. G01N 33/543
[52] U.S. Cl. ..................... 436/518; 422/63; 422/64; 422/67; 435/287.2; 436/45; 436/47; 436/50; 436/54; 436/527; 436/531; 436/807; 436/809
[58] Field of Search ................................. 422/63, 64, 72, 422/100, 67; 436/45, 47, 54, 518, 527, 531, 807, 809, 50; 435/71, 7.92, 7.93, 7.94, 7.95, 287, 289, 291

[56] References Cited

U.S. PATENT DOCUMENTS

| 3,437,447 | 4/1969 | Harmon ................................... 422/64 |
| 3,489,525 | 1/1970 | Natelson ................................. 422/64 |
| 3,615,230 | 10/1971 | Barnick et al. ......................... 422/64 |
| 3,615,236 | 10/1971 | Tamm ..................................... 422/64 |
| 3,677,091 | 7/1972 | Guigan ................................... 422/100 |
| 3,764,268 | 10/1973 | Kosowsky .............................. 422/64 |

(List continued on next page.)

FOREIGN PATENT DOCUMENTS

| 0289789 | 11/1988 | European Pat. Off. . |
| 3242460 | 5/1984 | Germany . |
| 3402304 | 7/1984 | Germany . |
| 3839080 | 6/1989 | Germany . |

OTHER PUBLICATIONS

Kunst et al (1988) "One–Step Enzyme Immunoassay . . . " Clin. Chem. 34(9) 1830–1833.
Patent Abstracts of Japan, v. 6, No. 104 (P–122) (982), Abstract of JP 57–35756(A).
ES 300 Brochure, Boehringer Mannheim, 1990.
ES 600 Brochure, Boehringer Mannheim.
Duncan et al., "The Boehringer Mannheim ES 300 Immunoassay System," Journal of Clinical Immunoassay, v12, No. 2 summer 1991. pp. 105–110.
Wolfschutz et al, "Automation of Dissolution Testing of Tablets and Capsules by Laboratory Robotics," Advances in Laboratory Automation Robotics 1986, Strmartis and Hawk Eds., Zymark Corporation, Hopkinton, MA 1987, pp. 139–152.

*Primary Examiner*—David Saunders
*Assistant Examiner*—Christopher L. Chin
*Attorney, Agent, or Firm*—Nikaido, Marmelstein, Murray & Oram

[57] ABSTRACT

The unit has three rotors, namely a reagent rotor (1), a sample rotor (2) and a reaction rotor (3). Each rotor has seats for vessels, which are arranged in circles about the respective rotor axis. At least two of the rotors (1, 2) are arranged concentrically to one another. The rotors can be brought into a plurality of rotating positions in which at least one of the openings (5b, 7b, 8b) is located in a predetermined liquid handling position (LH position).

A liquid handling unit (LH unit) comprises a liquid transfer needle (18) which is movable by a transfer needle moving apparatus in such a way that the movement path (23) crosses at least one LH position of each circle of openings (5b, 7b, 8b) on each rotor (1, 2, 3).

It thus become possible with a simply designed layout to carry out a wide range of heterogeneous immunological analyses in a flexible manner.

18 Claims, 4 Drawing Sheets

U.S. PATENT DOCUMENTS

| | | | |
|---|---|---|---|
| 3,836,329 | 9/1974 | Jordon | 422/100 |
| 3,969,079 | 7/1976 | Catarious et al. | 422/64 |
| 4,166,094 | 8/1979 | Froehlich et al. | 422/64 |
| 4,234,540 | 11/1980 | Ginsberg et al. | 422/64 |
| 4,259,289 | 3/1981 | Curry et al. | 422/64 |
| 4,341,736 | 7/1982 | Drbal et al. | 422/100 |
| 4,344,768 | 8/1982 | Parker et al. | 422/64 |
| 4,540,549 | 9/1985 | Manabe | 422/64 |
| 4,774,055 | 9/1988 | Wakatake et al. | 422/64 |
| 4,803,050 | 2/1989 | Mack | 422/100 |
| 4,837,159 | 6/1989 | Yamada | 422/67 |
| 4,879,242 | 11/1989 | Tsukioka | 436/54 |
| 4,908,186 | 3/1990 | Sakamaki | 422/64 |
| 5,104,808 | 4/1992 | Laska et al. | 422/67 |
| 5,175,086 | 12/1992 | Takekawa et al. | 436/47 |

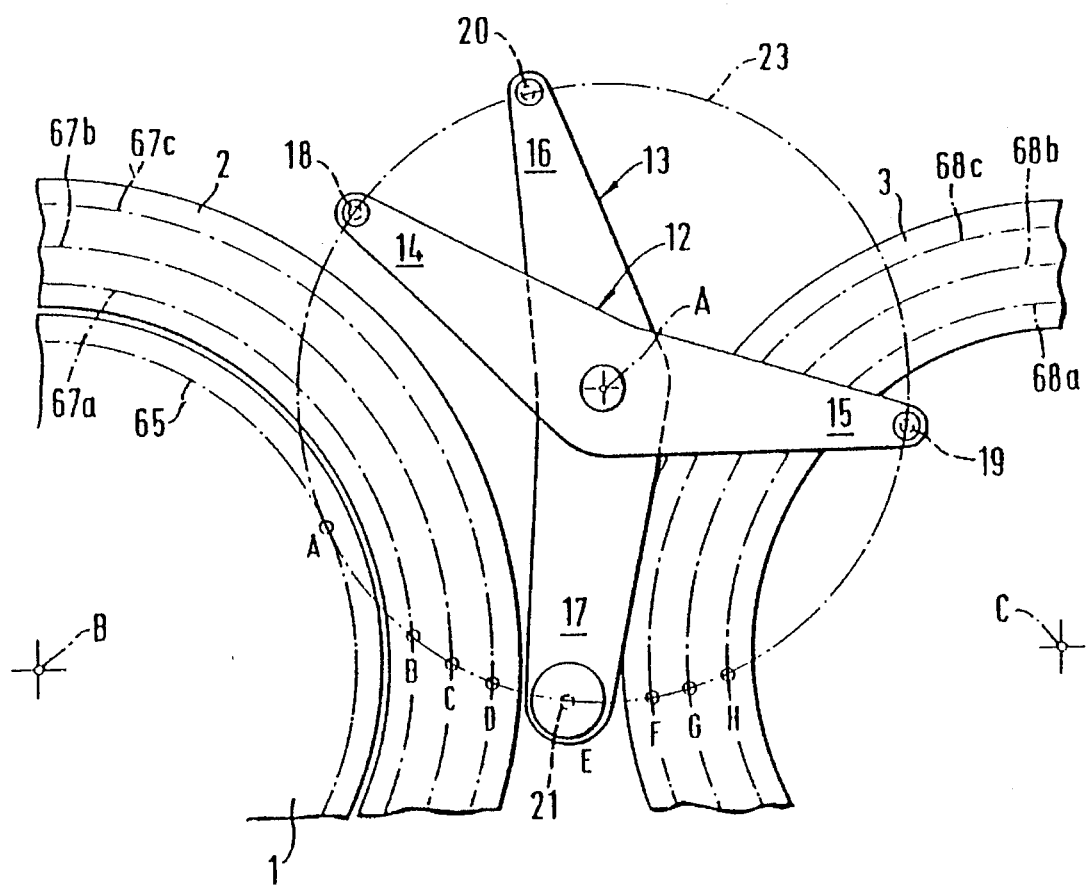

ANALYSER UNIT FOR HETEROGENEOUS IMMUNOLOGICAL TESTS

This application is a division of application Ser. No. 07/874,996, filed Apr. 24, 1992; now abandoned, which is a continuation of U.S. Ser. No. 07/551,827, filed Jul. 12, 1990; now abandoned.

The invention relates to an analyser unit for heterogeneous immunological tests.

Immunological determinations have great importance in medical analytical procedures. They are based on the highly specific binding reaction between immunological binding partners, for example an antigen and the corresponding antibody, and are therefore exceptionally selective and sensitive.

The immunological analysis methods very often call for separation between a bound and a free portion of a reaction component. This separation ("bound-free-separation", "BF separation") is effected in the case of heterogeneous immune tests by fixing a binding partner onto a carrier, use being made as carrier in particular of the reaction vessel itself (so-called "coated tubes") or balls of an inert plastics material. The BF separation requires intensive washing of the carrier in order to ensure that the free reaction partner has been completely removed from the carrier. The long incubation times associated with the heterogeneous reaction process are another characteristic of heterogeneous immunological tests.

Units for carrying out such analyses have to meet far more stringent requirements than conventional analyser units. Not only liquid reagents, but also the carriers (coated tubes or balls or the like), have to be available at the correct time and at the correct place. The washing represents an additional operating step, which usually has to be repeated several times and be incorporated in the equipment organization in a suitable manner. The incubation time, which is protracted and dependent on the respective analysis (the "test parameter"), not only increases the total time required, but causes great organizational problems in the case of analyser units which can perform several different analyses in one operating step (multi-parameter units), particularly if sample-selective operation is desired, i.e. the aim is to permit an arbitrary range of analyses for a sample contained in a single sample vessel. It is advisable, for example, to initiate first of all the analysis reactions with the longest incubation times (typically up to several hours) and fit in the tests with a shorter incubation time-span during the first incubation period. This involves dealing with a large number of mutually overlapping tests, and their handling therefore makes very great demands on the unit in terms of organization.

Since the manual performance of immunological tests is very cumbersome, there has long been a need, despite these high demands, to mechanise immunological tests as fully as possible.

A unit permitting a large number of immunological determinations to be handled fully automatically for various parameters is supplied by the assignee under the title "Enzymuntest-System ES 600". The unit has a stationary incubator in which up to 600 coated tubes can be incubated. They can be removed from the incubator by means of a drive similar in operation to a portal crane and transferred as required, under the control of a suitable control program, into a handling rotor. The handling rotor is small and rapidly rotatable. Around it are arranged, stationary, a washing point and an evaluating means. Stationary must be understood in the sense that the respective tubes for supplying or removing liquid, which are termed below "needles", are movable exclusively vertically in order to immerse them in the reaction vessels. This unit is provided with two concentric rotors for the samples and reagents. The liquids are transferred by means of a transfer needle movable on an arm not only vertically, but also parallel to the working plane of the unit. Although this unit is highly efficient, it requires a complicated arrangement and construction in particular for the transfer of the reaction vessels into the reaction rotor and for the drive and control of the reaction rotor.

In DE-A 34 02 304 there is described a unit in which the reaction vessels are arranged in a reaction rotor which is rotatable intermittently with a given division. The reaction vessels are arranged in a circle about the rotor axis at a distance which corresponds to the step size of the rotor movement. Balls act as carriers for a carrier-fixed immunological reagent and are introduced into the reaction vessels at a carrier addition station. The remaining handling stations (washing station, reagent feed stations, evaluating station) are also arranged around the reaction rotor and are stationary. The sample feed takes place by means of a transfer needle movable parallel to the rotor plane, and the samples are stored in a mobile magazine or in a sample rotor. The reaction rotor can also have three rows of reaction vessels, with stationary washing and reagent feed stations being assigned to each row. This known unit has a relatively simple construction. However, it is intrinsically too inflexible to be adapted to a large number of different analyses.

The object of the invention is therefore to make the efficient mechanization of heterogeneous immunological determinations possible, thereby enabling a large number of different, fully mechanized analytical determinations to be carried out and permitting flexible adaptation of the unit to a wide range of heterogeneous immunological test principles and test procedures. This is to be achieved with comparatively low expense with respect to the mechanical construction. The analysis unit according to the invention has three rotors, namely a sample rotor, a reagent rotor and a reaction rotor, each of which has seats for corresponding vessels, i.e. sample vessels, reagent vessels and reaction vessels. The vessels have openings in their tops for the supply and sampling of liquids. The seats for the vessels are arranged so that the openings are each located in a circle about the rotor axis. The reagent rotor and the sample rotor each have at least one such circle, in the case of the reaction rotor several rows of reaction vessels are provided, whose openings are arranged in several concentric circles about the rotor axis. The reaction vessels have inner walls coated with a binding partner, e.g. an antibody, polyhapten or streptavidin. At least two of the rotors are concentric to one another. The rotors are each rotatable into a plurality of rotating positions in which at least one of the openings is located in a predetermined position which serves for the supply or sampling of liquid and is therefore described as the liquid handling position (LH position).

The transfer of liquids, in particular sample and reagent, is carried out by a liquid handling unit (LH unit) with a transfer needle movable between the rotors. A moving apparatus serves for this purpose, which is designed so that the movement path of the needle crosses at least one LH position of each circle of openings on each rotor in such a way that the needle can be lowered into the respective opening.

A washing unit is also provided for flushing the inside of reaction vessels introduced into the reaction rotor with the aim of separating carrier-fixed reaction components contained there from the free reaction components. An evaluating device serves to measure a physical change characteristic of the analysis. This is preferably by evaluation of optical absorption at a particular wave-length, but the invention is not limited to a particular test principle, for example reflection photometry or fluorescence measurement could also be used.

The combination of these measures results in a unit which on the one hand is of comparatively simple construction and on the other enables a wide range of heterogeneous immunological analyses to be performed in an extremely flexible manner. Only a small amount of space is required, so that the unit can be designed as a desk top unit. The short conveyance paths make a rapid handling cycle and hence a high equipment throughput possible. Both sample-selective and reagent-selective operation are feasible.

The washing unit can in the most general case be provided stationary at the periphery of the reaction rotor. The washing needle of the washing unit is however particularly preferably movable by means of a washing needle moving apparatus on a movement path which crosses in each case an LH position of each circle of reaction vessel openings on the reaction rotor. A single washing unit can therefore be used for the BF separation in all the reaction vessels. The movement path of the washing needle particularly preferably coincides at least partially with the movement path of the liquid transfer needle, with the same LH positions on the reactor rotor being crossed both by the movement path of the transfer needle and by that of the washing needle. This simplifies the design and makes it possible to perform liquid transfer operations and washing operations in direct succession without rotor movement.

The evaluating instrument can be provided stationary at the periphery of the reaction rotor, the liquid in the reaction vessels themselves being evaluated in the simplest case. In the case of photometry, for example, the light beam of a photometer can cross the transport path of the reaction vessels on the reaction rotor.

If liquid from the reaction vessels is sampled for evaluation and the evaluating device for this purpose comprises a suction needle, a moving apparatus is preferably also provided for the suction needle. Its movement path also preferably crosses an LH position of each circle of reaction vessel openings on the reaction rotor. In this case also it is advantageous if the movement path of the suction needle coincides at least partially with the movement path of the liquid transfer needle.

The moving apparatuses for the transfer needle, and where applicable for the washing needle and the suction needle, can take various forms. For example, a transport rail can be provided which runs between the rotors parallel to their surface. The needles can be moved to and fro on this rail by means of power driven travellers. Another possibility would be the use of bent robot arms to which the needles are fixed. The required movements can be made in a surprisingly simple manner by means of swivel arms, as explained in detail below.

The invention will be explained in detail below with reference to an exemplifying embodiment represented diagrammatically in the figures, where FIG. 1 is a portion of an analyser unit viewed in perspective;

FIG. 3 to FIG. 5 are views of a unit according to the invention in diagrammatic form for explaining the functional sequence.

Figure 1:
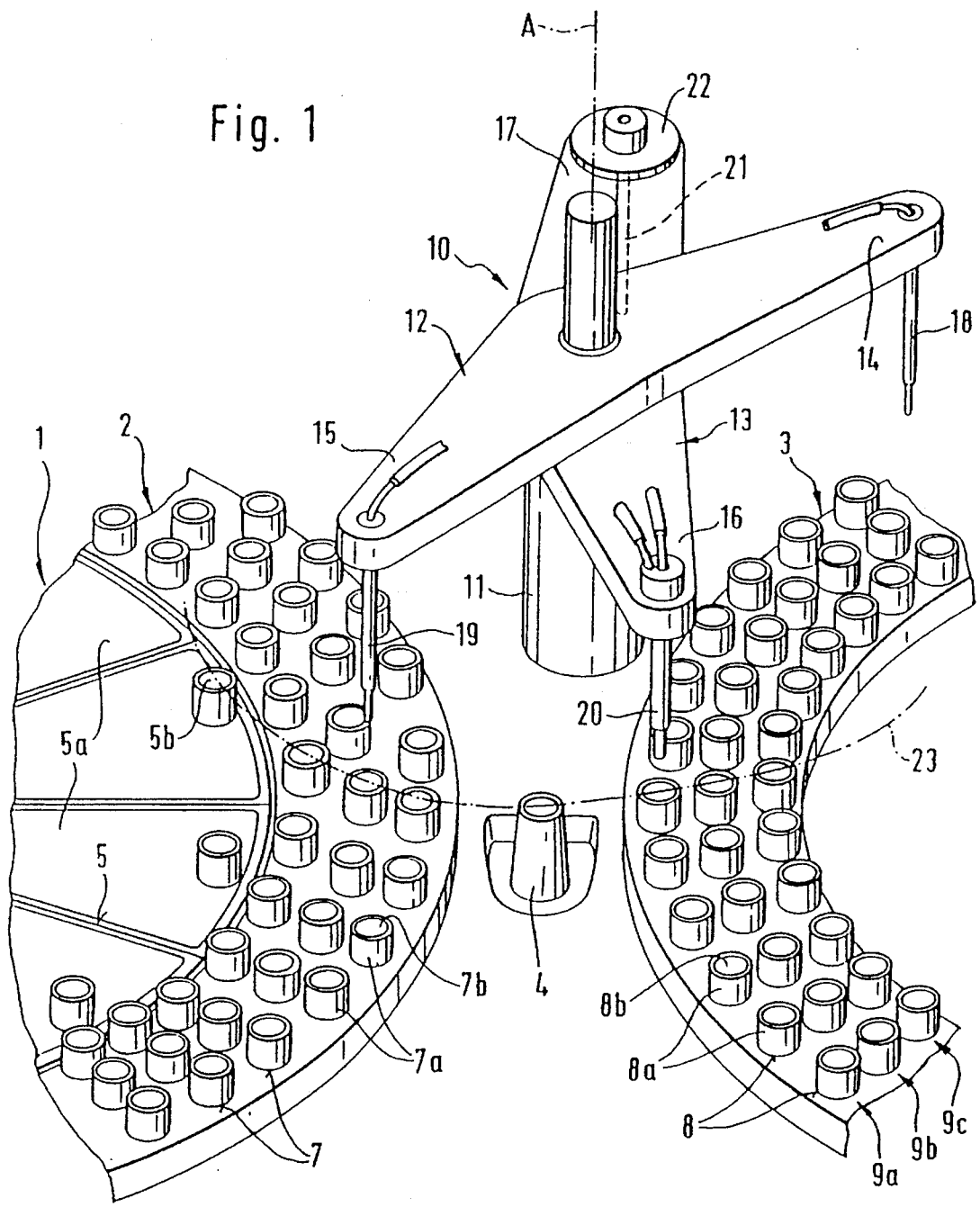

The unit represented in FIG. 1 has a reagent rotor 1, a sample rotor 2 and a reaction rotor 3, the reagent rotor and the sample rotor being arranged concentrically to each other so that they form a double rotor, the rotors of which are nevertheless rotatable independently of one another. A washing vessel 4 is located between the double rotor 1, 2 and the reaction rotor 3.

Each of the rotors has seats for vessels. The reagent rotor 1 has preferably comparatively large seats 5 for a comparatively small number of reagent vessels 5a with openings 5b.

The sample rotor 2 has with advantage circular seats 7 for sample vessels, which in the represented case are arranged in three concentric circles. They serve to accommodate sample vessels 7a with openings 7b. The seats 8 for the reaction vessels 8a with openings 8b in the reactor rotor 3 are advisably circular and arranged in several rows.

In the region between the rotors there is located a multifunction liquid handling unit (MFLH unit) designated overall as 10. It consists in the represented preferred embodiment mainly of a column 11 and two swivelling carriers 12 and 13 each with two carrying arms 14,15 and 16,17.

A transfer needle 18, 19 is attached to each of the carrying arms 14, 15 of the first swivelling carrier 12. The second swivelling carrier 13 carries on its first carrying arm 16 a washing needle 20 and on its second carrying arm 17 a suction needle 21 for a photometer, this suction needle 21 being in FIG. 1 concealed by the carrying arm 17 and therefore represented by dashes. A vibration drive 22 serves to set the needle 21 vibrating in order to mix a liquid thoroughly in which it is immersed.

The swivelling axis A of the MFLH unit runs parallel with the axes of rotation of the rotors 1, 2,3 and hence perpendicular to the working plane of the unit, which is defined by the rotors. The needles 18, 19, 20, 21 are all fixed at the same distance from the axis A so that they all move on the same swivelling circle 23. The needles therefore have—relative to the working plane of the unit—the same movement path. The washing vessel 4 also lies on the swivelling circle 23.

The MFLH unit also enables the required raising and lowering of the needles 18–21 to be carried out in a direction perpendicular to the working plane. To this end a separate or—preferably— common lift drive is provided for both swivelling carriers 12, 13.

The rotors 1, 2, 3 are in each case rotatable in a plurality of rotating positions, in which at least one of the openings 5b, 7b, 8b of the respective vessels 5a, 7a, 8a is in a position which lies on the swivelling path of the needles 18–21. In this position, which is termed the LH position, each of the needles 18–21 can optionally be lowered into the respective openings in order to sample liquid, feed liquid etc., i.e. to perform liquid handling operations in general.

In order to make the shortest possible movement paths of the moving apparatus for the various needles possible, it is advisable if, as represented, the reaction rotor is arranged radially outwards from the double rotor 1, 2. In the represented exemplifying embodiment its axis of rotation is different from that of the double rotor. It may also be appropriate however to design all three rotors concentric, i.e. with a common axis of rotation.

Figure 2:
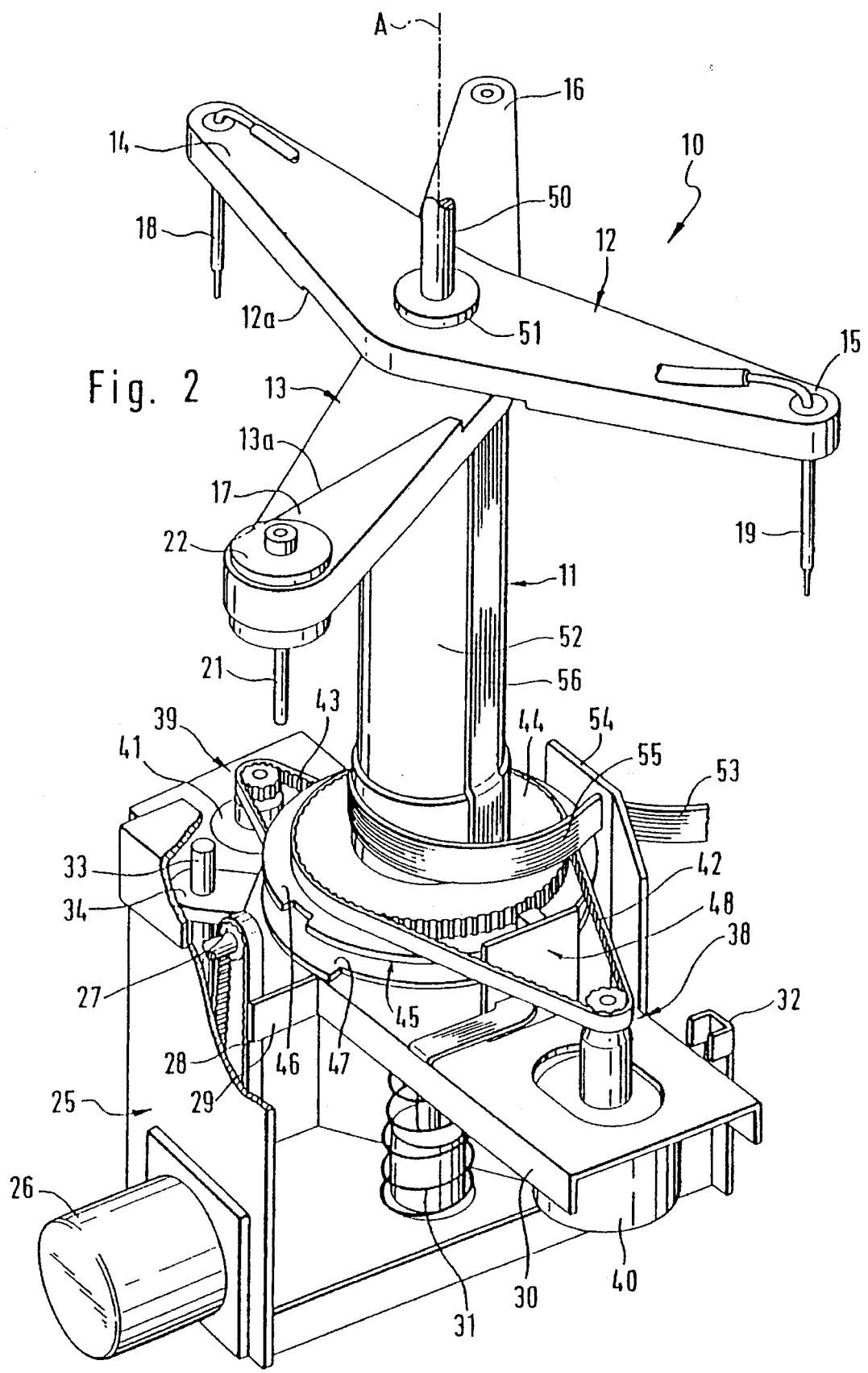
FIG. 2 is a multi-function liquid handling unit for an analyser unit according to the invention viewed in perspective.

The swivelling carriers 12, 13 have preferably separate rotation drives and a common lift drive. An example is shown in detail in FIG. 2.

The lift drive designated overall as 25 has a stepped motor 26 and a toothed belt 28 running over a roller 27. The toothed belt 28 is connected via a connection piece 29 to a common supporting frame 30 of the rotation drives, which is raised and lowered as a unit. A compression spring 31 is provided for balancing the masses. The vertical movement is monitored by means of a light-activated position sensing device 32 so that the height of the supporting frame 30 and hence of the swivelling carriers 12, 13 can be adjusted exactly independently of the drive play.

A control rod 33 and a self-aligning bearing 34 form a torque bracket by means of which rotation of the supporting frame 30 is prevented.

The rotation drives 38, 39 each have a stepped motor 40 and 41 and a toothed belt 42, 43. The toothed belts run drive-side on two toothed wheels 44, 45 to each of which a code disc 46, 47 is connected. A light-activated position sensing device 48 serves to monitor the rotational movement of the two code discs and hence of the swivelling carriers 12 and 13, so that the rotational position also of the arms can be adjusted very precisely independently of the play of the drive.

The column 11 consists in detail of a control column 50, an inner swivelling drive tube 51, which makes the connection between the rotation drive 39 and the first swivelling carrier 12, and an external swivelling drive tube 52 which forms the connection between the swivelling drive 38 and the second swivelling carrier 13.

The electrical and hydraulic connections to the needles at the ends of the carrying arms must naturally be arranged so that they can follow the swivelling movement without being damaged. The electrical connection can for example, as represented, be made by means of a first ribbon cable 53, a PCB connection 54 and a second ribbon cable 55 which passes into a section 56 fixed to the outer swivelling tube. The subsequent connecting wires to the needles 18–21 are omitted for the sake of clarity.

The hydraulic lines are likewise only suggested for the sake of clarity. The rotational movement can for example be balanced out by running the hoses in spiral form inside the swivelling drive tube 51.

The swivelling movement of the swivelling carriers 12, 13 is limited overall to less than 360' by a stop (not represented). Stop faces 12a, 13a are also provided on each of the carriers, which limit movement of the swivelling carriers relative to one another.

Figure 3:
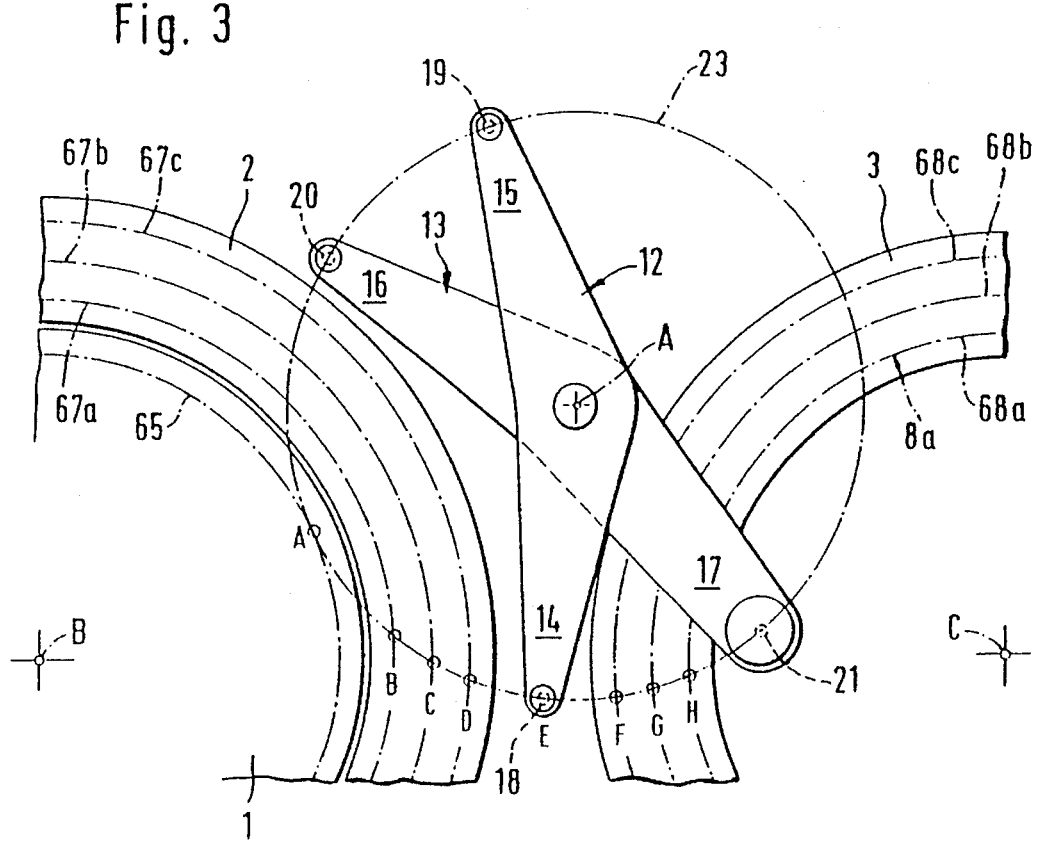

The function of the analyser unit will be explained in detail below with reference to FIGS. 3–5. These show in a highly schematized view the reagent rotor 1, the sample rotor 2, the reaction rotor 3 and the swivelling carriers 12 and 13.

The openings (not represented here) of the reagent vessels are arranged on a circle 65, shown in dots and dashes, about the common axis B of the reagent rotor 1 and the sample rotor 2. The openings of the sample vessels run in circles 67a, 67b, 67c about the axis B. The openings of the three reaction vessel rows are located correspondingly in circles 68a, 68b, 68c about the axis C of the reaction rotor 3. The LH positions of the rotors are marked as A, B, C, D, F, G, H. The position of the washing vessel bears the reference symbol E.

It should be pointed out in this connection that the seats 7 and 8 on rotors comprising several rows lying in concentric circles do not necessarily—as represented in FIG. 1—have to be arranged so that in a single rotational position of the rotor one vessel opening of each row lies on the movement path 23. Rather is it sufficient if the respective opening of that vessel at which a liquid handling operation is to be carried out can be brought into the corresponding LH position.

The method of operation of the unit will be described below with reference to a two-step sandwich test for determining an antigen Ag from the sample, which incorporates the following steps:

a) A reaction vessel containing an antibody Ab specific for Ag in carrier-bound form (Abb) is placed on the reaction rotor 3. For example, a coated tube to the inside wall of which the antibody is bound is normally involved.

b) The reaction vessel is filled with a particular amount of sample and reagent.

c) Then the specific binding reaction between the Ag from the sample and the Abb is allowed to take place, in the course of which carrier-bound complexes Abb-Ag form. This requires a fairly long time in many cases, so that work steps involving other parameters are carried out by the unit in the meantime.

d) Suction and thorough washing then take place (BF separation).

e) Conjugate of a further antibody specific for the antigen with a labelling enzyme (AbE) is then added.

f) Renewed incubation for the formation of sandwich complexes Abb-Ag-AbE.

g) Renewed suction and washing; superfluous AbE is thereby separated from the bound phase (BF separation).

h) Addition of a colour-forming substrate whose colour change is characteristic of the concentration of the labelling enzyme E.

i) Mixing, suction and photometering.

This test sequence is known from the literature and therefore does not need to be described in detail. There are also numerous other test procedures for heterogeneous immunological determinations. A particular advantage of the present unit consists in the fact that it permits the implementation of numerous different immunological test principles with simple means.

Figure 4:
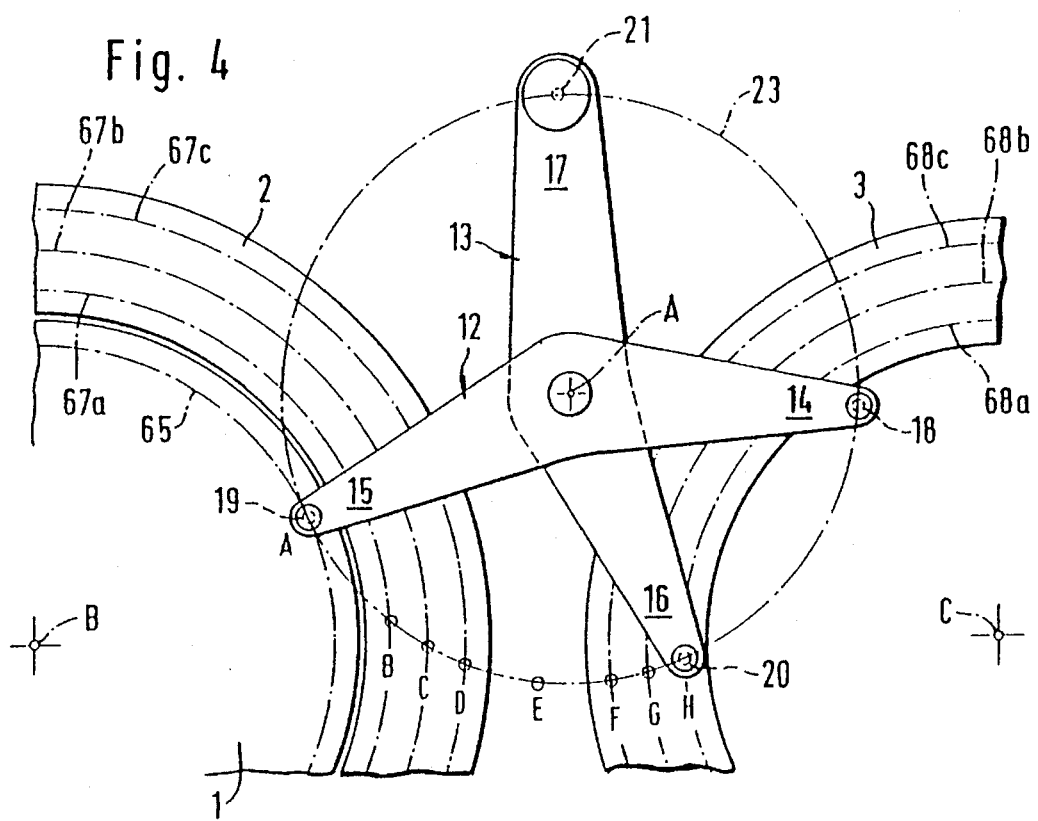

The individual steps of a two-step sandwich test are performed by the unit according to the invention as follows:

a) Depending on the number of analyses to be performed the reaction vessels (coated tubes) required are placed on the seats of the rotor 3. In so doing it is advisable for the reaction vessels for a particular test to be arranged close to one another in blocks so that the individual steps can be carried out successively (batch-wise) for all the reaction vessels of a particular test. This is simplified in the case of the present unit by the fact that all the handling functions are carried out at the same LH positions F, G, H and the movement path of the washing needle 20 and the suction needle 21 coincides with that of the liquid transfer needles 18, 19, so that they cross the reaction vessel rows at the same LH positions F, G, H.

b) Suction by means of the first liquid transfer needle 18 of reagent first of all in the LH position A and of sample in one of the positions B, C or D then takes place. After the collection of reagent and sample, the transfer needle 18 is washed on the outside in position E in each case. Sample and reagent are ejected in one of the positions F, G or H into the corresponding reaction vessel. In so doing the second swivelling carrier 13 is advisably located in the parked position shown in FIG. 3, while the first swivelling carrier 12 travels along the movement path from A to F, G or H. If—as with the represented preferred embodiment—the lift drive is common for both swivelling carriers, the second swivelling carrier not currently in use must be located in a position in which its needles during lowering cannot knock into anything or penetrate into any of the vessel openings. Such a position is shown in FIG. 3.

c) During the incubation the rotor 3 is advisably brought into another position in which another block of reaction vessels is located in the vicinity of the LH positions F, G, H and can be handled.

d) FIG. 4 shows the unit in an operating state in which the washing needle 20 located on the carrying arm 16 is lowered into a reaction vessel located in the LH position H in order to wash the latter. Suitable designs for the washing needle are known. For example it can be designed as a double tube, with washing liquid being sprayed into the reaction vessel through one tube and aspirated through the other tube.

e) The subsequent addition of conjugate could take place in principle by means of the same liquid transfer needle 18 with which sample and reagent in step b have been metered, it being essential that washing takes place in each case in position E to avoid carry-over. If however according to the represented preferred embodiment the washing needle 20 and the suction needle 21 are fixed to a common swivelling carrier 13 and the movement path of the liquid transfer needle 18 in the vicinity of the LH positions F, G, H coincides with that of the washing needle 20 and suction needle 21, the liquid transfer needle 18 cannot simply be passed by the washing needle. In this case it is advisable if, as represented, a second carrying arm 15 with a second liquid transfer needle 19 is provided on the first swivelling carrier 12. In this way it is possible to aspirate the conjugate from the corresponding reaction vessel at the LH position A during the washing and then transfer it into the corresponding LH position of the reaction rotor F, G, H.

f) During the following incubation another block of reaction vessels can be handled analogously to step c).

g) and h) The bound-free separation and the metering of the substrate take place analogously to steps d) and e) by means of the washing needle 20 and the second liquid transfer needle 19.

i) FIG. 5 shows that the first swivelling carrier 12 adopts during the photometering phase, in similar fashion to the second swivelling carrier 13 during the sample metering (step b, FIG. 3), a parking position in which the liquid transfer needles 18, 19 do not collide during the required lifting movements. The second swivelling carrier is shown in a position in which the suction needle 21 is located above the washing position E. From here it can be brought for aspiration and photometering, according to requirement, into one of the LH positions F, G and H.

The represented embodiment, in which two needles are located respectively on two carrying arms, is a particularly simple design and permits rapid and economic execution of many different immunological analyses. In this case the angles between the carrying arms 14, 15 and 16, 17 of the individual swivelling carriers 12 and 13 should be greater than 90°, preferably greater than 120°, in order to make the modes of operation described possible. Separate moving apparatuses for one or more liquid transfer needles, a washing needle and a suction needle can however also be provided. For example, one single-arm swivelling carrier each would be suitable, the swivelling carriers possibly being of different length and capable of being swivelled about different or (preferably) about the same swivelling axis.

It is also not essential that one circle of vessel openings should have only a single LH position. In the represented case, for example, it would obviously be possible to provide further LH positions where the circle 23 crosses the circles 67 a–c and 68 a–c a second time. This is less preferable, however, because very complicated rotor movements would be necessary in order to execute the individual reactions in the correct time sequence. This would require major expense on the instrument control (which is advisably undertaken by means of a microprocessor).

We claim:

1. A method of selectively performing a plurality of heterogeneous immunological tests in one run in a sample-selective operation in which for each sample contained in a particular sample vessel an arbitrary selection of analyses required for detection of an analyte is possible and wherein said tests comprise highly specific binding reactions of immunological binding partners, at least some of the binding reactions requiring substantially different incubation times, using an automatic analyzer that comprises:

a plurality of reagent vessels containing liquid reagents and having openings therein;

reagent rotor means having a reagent rotor axis for rotatably providing seats for the reagent vessels, with the reagent vessel openings arranged on at least one circle about the reagent rotor axis;

the reagent vessels located on the reagent vessel seats on the reagent rotor means;

a plurality of sample vessels containing liquid samples and having openings therein;

sample rotor means having a sample rotor axis for rotatably providing seats for the sample vessels, with the sample vessel openings arranged on at least one circle about the sample rotor axis;

the sample vessels located on the sample vessel seats on the sample rotor means;

a plurality of reaction vessels containing a carrier bound reagent which is specific for either the analyte or another specific binding reagent, and having openings therein;

reaction rotor means having a reaction rotor axis for rotatably providing seats for the reaction vessels, with the reaction vessel openings arranged on a plurality of concentric circles about the reaction rotor axis;

the reaction vessels located on the reaction vessel seats on the reaction rotor means;

wherein at least two of the sample, reagent and reaction rotor means are arranged concentric to one another;

liquid handling means for transferring reagents and samples between the plurality of reagent, sample and reaction vessels, the liquid handling means including a transfer needle means movable along a movement path which crosses each of said circles of openings of said reagent vessels, sample vessels and reaction vessels for transferring liquid from one vessel to another;

a washing means including a washing needle for individually washing single reaction vessels on said rotor by introducing liquid thereinto and suctioning liquid therefrom; and a detection means at the periphery of said reaction rotor means including a liquid sampling suction needle said method comprising the steps of:
(a) rotating the sample vessel rotor means into a liquid handling position in which said movement path of said transfer needle means crosses said circle of sample vessels, and transferring a liquid sample from a sample vessel to the liquid handling means;

(b) rotating the reaction vessel rotor means into a liquid handling position in which said movement path of said transfer needle means crosses said circle of reaction vessels, and transferring the liquid sample from the liquid handling means to one of the reaction vessels of the reaction vessel rotor means;

(c) rotating the reagent vessel rotor means into a liquid handling position in which said movement path of said transfer needle means crosses said circle of reagent vessels, and transferring a liquid reagent from the reagent vessel to the liquid handling means, the liquid reagent including a conjugate of an immunological binding partner specific for said analyte or another specific binding reagent in said reaction vessel and a label;

(d) transferring the liquid reagent from the liquid handling means to the reaction vessel having the liquid sample therein while the reaction vessel rotor means is in said liquid handling position in which said transfer needle means crosses said circle of reaction vessels;

(e) mixing the liquid sample and the liquid reagent in said reaction vessel;

(f) incubating the reaction vessel contents while on the reaction vessel rotor while maintaining the reaction vessel at a preselected temperature for a preselected period of time;

g) rotating said reaction rotor means and plural circles of reaction vessels thereon into a washing position, lowering said washing needle of said washing means into a single reaction vessel, and washing the contents of that reaction vessel by introducing a wash liquid therein and suctioning liquid therefrom to effect separation of a carrier bound and a free reaction component of the reaction in the reaction vessel;

(h) adding a detection reagent to the reaction vessel so as to produce an observable change by a reaction of the label with the detection reagent; and (i) rotating said reaction rotor means into a detection position and lowering the liquid sampling suction needle of said detection means into said reaction vessel and suctioning liquid therefrom; and (j) detecting an observable change of said liquid caused by said reaction of said detection reagent with said label by sampling of liquid from an individual reaction vessel on the reaction rotor, evaluating the sampled liquid, and correlating the observable change to the presence of analyte in the liquid sample; wherein said steps (a) to (e) are performed consecutively in a series of analyses of different samples with respect to the same heterogeneous immunological test and wherein, during performing said step (f) with respect to a first heterogeneous immunological test of at least one sample, steps (a) to (e) are performed with respect to a second heterogeneous immunological test of at least one sample which second immunological test is different from the first heterogeneous immunological test.

2. A method for selectively performing a plurality of heterogeneous immunological tests in one run according to claim 1, wherein said step (g) includes moving the washing needle on at least a portion of a movement path which crosses a liquid handling position of each circle of reaction vessel openings on the reaction rotor means.

3. A method for selectively performing a plurality of heterogeneous immunological tests in one run according to claim 1, wherein said step (i) includes moving the liquid sampling suction needle on at least a portion of a movement path which crosses a liquid handling position of each circle of reaction vessel openings on the reaction rotor means.

4. A method of selectively performing a plurality of heterogeneous immunological tests in one run according to claim 1, wherein said step (j) of detecting the observable change in each of the reaction vessels includes the step of evaluating the reaction by measuring optical absorption at a particular wave-length.

5. A method of selectively performing a plurality of heterogeneous immunological tests in one run according to claim 1, wherein the label is a fluorescence label and said step of evaluating the observable change in each of the reaction vessels includes the step of evaluating the reaction by measurement of fluorescence.

6. Method of claim 1, wherein the liquid handling means, the washing means, and the detection means travel in circular movement paths which cross each of said circles of openings of said reagent vessels, sample vessels and reaction vessels, with the transfer needle means, washing means and detection means moving about an axis located at the center of the respective circular movement paths, wherein the axis of the liquid handling means, the axis of the washing means, and the axis of the detection means is substantially the same axis.

7. Method of claim 1, wherein the reaction rotor means is rotated in a plurality of directions during the performance of the one run of heterogeneous immulogical tests.

8. Method of claim 1, wherein the insides of the reaction vessels are coated with said solid phase bound reagent.

9. A method of selectively performing a plurality of heterogeneous immunological tests in a sample-selective operation in which for each sample contained in a particular sample vessel an arbitrary selection of analyses required for said sample for detection of an analyte is possible and wherein said tests comprise highly specific binding reactions of immunological binding partners, at least some of the binding reactions requiring substantially different incubation times, said method comprising the steps of:

(a) rotating a sample vessel rotor about a sample vessel rotor axis, the sample vessel rotor containing a plurality of sample vessels containing liquid samples and having openings therein, with the sample vessel openings being arranged on at least one circle about the sample vessel rotor axis, to place a preselected sample vessel at a sample vessel liquid handling position;

(b) transferring a liquid sample from the sample vessel at the sample vessel liquid handling position to a liquid handler;

(c) rotating a reaction vessel rotor about a reaction vessel rotor axis, the reaction vessel rotor containing a plurality of reaction vessels each reaction vessel having a solid phase bound reagent immobilized on an interior wall which is specific for an analyte in the liquid sample or for another specific binding agent, said reaction vessels each having an opening therein, the reaction vessel openings being arranged on a plurality of concentric circles about the reaction vessel rotor axis, to place a preselected reaction vessel at a reaction vessel liquid handling position;

(d) transferring the liquid sample from the liquid handler to the reaction vessel on the reaction vessel rotor at the reaction vessel liquid handling position;

(e) rotating a reagent vessel rotor about a reagent vessel rotor axis, the reagent vessel rotor containing a plurality of reagent vessels containing liquid reagents and having openings therein, the liquid reagent including a conjugate of an immunological binding partner and a label, wherein the conjugate in the liquid reagent is specific for said analyte or another specific binding reagent in the reaction vessel, the reagent vessel openings arranged on at least one circle about the reagent rotor axis, to place a preselected reagent vessel at a reagent vessel liquid handling position;

(f) transferring liquid reagent from the reagent vessel at the reagent vessel handling position to a liquid handler;

(g) transferring the liquid reagent in the liquid handler to the reaction vessel having the liquid sample therein while the reaction vessel is at the reaction vessel liquid handling position;

(h) mixing the liquid sample and the reagent liquid in the reaction vessel (i) incubating the reaction vessel contents while on the reaction vessel rotor while maintaining the contents at a preselected temperature for a preselected period of time to react the liquid sample, the liquid reagent and the solid phase bound reagent to produce bound and free reaction components;

(j) separating bound and free reaction components of the reaction in the reaction vessel by washing and suctioning the reaction vessel contents through a washing device which travels about an axis on a circular path, each liquid handler also traveling about an axis on a circular path, the circular paths crossing each of said circles of openings of the reagent vessels, sample vessels and reaction vessels, the axis of the washing device and the axis of each liquid handler being substantially the same axis;

(k) adding a detection reagent to the reaction vessel to produce an observable change by reaction of the detection reagent with bound label; and (l) detecting and correlating the observable change to the presence of analyte in the liquid sample;

wherein during the plurality of immunological tests step (i) of a first immunological test is performed in one reaction vessel at the same time that steps (a) to (g) of a second immunological test are performed in a second reaction vessel.

10. The method of claim 9, further comprising the steps of:

(m) selecting a first set of at least one first sample vessel, at least one first reaction vessel and at least one first reagent vessel, said selection being adapted for a first heterogeneous immunological test, (n) performing steps (a) to (g) in the first reaction vessel with at least one sample from said first sample vessel using reagent from the first reagent vessel (o) selecting a second set of at least one second sample vessel, at least one second reaction vessel and at least one second reagent vessel, said selection being adapted for a second heterogeneous immunological test differing from said first heterogeneous immunological test (p) and performing steps (a) to (g) of the second set, with sample from the second sample vessel and reagent from the second reagent vessel, with the reaction vessel of steps (d) and (g) being the second reaction vessel, during the step (i) of incubating the first reaction vessel of the first set for the preselected period of time.

11. The method of claim 9, wherein at least two of the rotors of steps (a), (c) and (e) are rotated concentrically.

12. The method of claim 9, wherein the liquid handler of at least one of steps (b), (d) or (f) comprises a transfer needle, and steps (b), (d) and/or (f) include moving the transfer needle along at least a portion of a movement path which crosses the at least one circle of sample vessel openings, the plurality of concentric circles of reaction vessels openings, and the at least one circle of reagent vessel openings, with the locations where the transfer needle movement path crosses the circles defining a respective liquid handling position.

13. The method of claim 12, wherein step (l) includes the steps of moving a liquid sampling suction needle along at least a portion of a movement path of said liquid transfer suction needle which crosses said circle of reaction vessels openings on the reaction vessel rotor, transferring liquid to be evaluated for observable change from the reaction vessel via the liquid sampling suction needle to a detection location wherein the observable change is detected.

14. The method of claim 13, wherein the liquid sampling suction needle of step (l) is moved on a movement path which at least partially coincides with the transfer needle movement path, with the same liquid handling positions on the reaction vessel rotor being crossed by both the transfer needle movement path and the liquid sampling suction needle movement path.

15. The method of claim 9, wherein the separating step (j) is accomplished by moving a washing needle along at least a portion of a movement path which crosses a liquid handling position of each circle of reaction vessel openings, and includes washing and suctioning the contents of the reaction vessel.

16. The method of claim 15, wherein the washing needle movement path at least partially coincides with the transfer needle movement path, with the same liquid handling positions on the reaction vessel rotor being crossed by both the transfer needle movement path and the washing needle movement path.

17. Method of claim 16, wherein the transfer needle movement path and the washing needle movement path are the same.

18. Method of claim 8, wherein step (j) of separating bound and free reaction components is accomplished by moving the reaction vessel into a washing position and lowering a washing needle into only that reaction vessel and no other reaction vessels to wash the reaction vessel components to effect a separation of said components.

* * * * *